(12) United States Patent
Hogan

(10) Patent No.: US 10,102,424 B2
(45) Date of Patent: Oct. 16, 2018

(54) METHOD AND SYSTEM FOR DOCUMENT AUTHENTICITY VERIFICATION

(71) Applicant: Joshua Noel Hogan, Los Altos, CA (US)

(72) Inventor: Joshua Noel Hogan, Los Altos, CA (US)

(*) Notice: Subject to any disclaimer, the term of this patent is extended or adjusted under 35 U.S.C. 154(b) by 0 days.

(21) Appl. No.: 15/218,348

(22) Filed: Jul. 25, 2016

(65) Prior Publication Data

US 2017/0024909 A1    Jan. 26, 2017

Related U.S. Application Data

(60) Provisional application No. 62/197,079, filed on Jul. 26, 2015.

(51) Int. Cl.
| | |
|---|---|
| *G06K 9/00* | (2006.01) |
| *G01N 21/47* | (2006.01) |
| *G07D 7/12* | (2016.01) |
| *B42D 25/425* | (2014.01) |
| *B42D 25/36* | (2014.01) |
| *B42D 25/47* | (2014.01) |

(52) U.S. Cl.
CPC ......... *G06K 9/00442* (2013.01); *B42D 25/36* (2014.10); *B42D 25/425* (2014.10); *B42D 25/47* (2014.10); *G01N 21/47* (2013.01); *G07D 7/12* (2013.01)

(58) Field of Classification Search
USPC .................. 382/100, 131, 108; 340/5.86
See application file for complete search history.

(56) References Cited

U.S. PATENT DOCUMENTS

| | | | | |
|---|---|---|---|---|
| 6,584,214 | B1 * | 6/2003 | Pappu ...................... | G06K 9/00 340/5.86 |
| 6,801,346 | B2 * | 10/2004 | Schilling .............. | B42D 25/328 283/85 |
| 7,006,294 | B2 * | 2/2006 | Steenblik ............... | B82Y 20/00 359/619 |
| 7,526,329 | B2 | 4/2009 | Hogan | |
| 7,751,862 | B2 | 7/2010 | Hogan | |
| 2006/0231625 | A1 * | 10/2006 | Cumming .......... | G01N 21/3581 235/454 |
| 2014/0300896 | A1 * | 10/2014 | Froggatt ................ | G01N 21/45 356/342 |

* cited by examiner

*Primary Examiner* — Ishrat I Sherali

(57) ABSTRACT

The invention provides a system and method for secure document verification. In the preferred embodiment, embedded information consists of marks embedded in the interior of the document and are comprised of regions that have refractive index modified to carry information. In the preferred embodiment the marks are not discernable by conventional imaging, spectroscopic or optical polarization techniques, but are discernably by interferometric techniques, such as optical coherence tomography. Multiple alternate embodiments are taught.

2 Claims, 4 Drawing Sheets

METHOD AND SYSTEM FOR DOCUMENT AUTHENTICITY VERIFICATION

CROSS REFERENCES TO RELATED PATENTS OR APPLICATIONS

This application claims priority from U.S. provisional patent application No. 62/197,079, filed Jul. 26, 2015, the entirety of which is incorporated by reference as if fully set forth herein.

This invention is related to U.S. Pat. No. 7,526,329 titled Multiple reference non-invasive analysis system and U.S. Pat. No. 7,751,862 titled Frequency resolved imaging system, the contents of both of which are incorporated by reference herein as if fully set forth.

GOVERNMENT FUNDING

None

FIELD OF USE

The invention relates to non-invasive imaging and analysis techniques such as Optical Coherence Tomography (OCT). In particular it relates using optical interferometric techniques to monitor or measure sub-surface attributes of documents such as bank notes (paper currency), legal documents or documents containing highly confidential information.

BACKGROUND OF THE INVENTION

Non-invasive imaging and analysis of targets using optical coherence tomography (OCT) is a powerful technique for acquiring sub-surface information embedded in targets without damaging the target or system being analyzed.

The embedded information in a particular sheet of paper of base document can be imaged and analyzed by Optical coherence tomography (OCT), a technology for non-invasive imaging and analysis. There are more than one OCT techniques. Time Domain OCT (TD-OCT) typically uses a broadband optical source with a short coherence length, such as a super-luminescent diode (SLD), to probe and analyze or image a target.

Multiple Reference OCT (MRO) is a version of TD-OCT that uses multiple reference signals. Another OCT technique is Fourier Domain OCT (FD-OCT). A version of Fourier Domain OCT, called Swept Source OCT (SS-OCT), typically uses a narrow band laser optical source whose frequency (or wavelength) is swept (or varied) over a broad wavelength range. In TD-OCT systems the bandwidth of the broadband optical source determines the depth resolution. In SS-OCT systems the wavelength range over which the optical source is swept determines the depth resolution.

Another version of Fourier Domain OCT, often referred to as Spectral Domain OCT (SD-OCT), typically uses a broad band optical source and a spectrometer to separate out wavelengths and detect signals at different wavelengths by means of a multi-segment detector.

OCT depth scans can provide useful sub-surface information including, but not limited to: sub-surface images of regions of targets; measurement of thickness of layers of targets. More generally OCT depth scans can provide useful sub-surface information regarding attributes of targets.

Documents, such as bank notes and legal documents require security features to protect against counterfeit documents. There is an on-going need for improved protection of valuable documents against counterfeiting. The ability of OCT to analyze information embedded within a target enables adding a security layer to documents by embedding information or data during the manufacturing process of the paper (or base document).

BRIEF SUMMARY OF THE INVENTION

The invention meets at least all of the unmet needs cited hereinabove.

The invention provides a system and method for secure document verification.

In the preferred embodiment, embedded information consists of marks embedded in the interior of the document and are comprised of regions that have refractive index modified to carry information. In the preferred embodiment the marks are not discernable by conventional imaging, spectroscopic or optical polarization techniques, but are discernable by interferometric techniques, such as optical coherence tomography. Multiple alternate embodiments are taught.

In the case of valuable or legal documents, such as bank notes, information can be systematically encoded in a manner that is difficult to reproduce, thereby providing additional barriers to counterfeiting. In the preferred embodiment the embedded information consists of marks embedded in the interior of the document and are comprised of regions that have refractive index modified to carry information. In the preferred embodiment the marks are not discernable by conventional imaging, spectroscopic or optical polarization techniques, but are discernable by interferometric techniques, such as optical coherence tomography. In some embodiments the marks are systematically aligned spatially and constitute an encoded data sequence with error correction code-words. In some embodiments the marks are randomly spatially distributed in the manufacturing process of the paper of base document.

In the preferred embodiment, the method of uniquely identifying a document of interest, comprises the steps of a) embedding in the document at least one region where said region has a predetermined refractive index; and b) scanning, using an optical coherence tomography device, said document and measuring optical path length data signal obtained from said embedded region.

The invention also teaches a method of manufacturing a secure document base material for wherein document authenticity is ensured by embedded regions in said base material, where a first portion of said embedded regions having at least a first refractive index and a second portion of said embedded regions having at least a second refractive index, and where said first refractive index is not equal said second refractive index, such that said document authenticity is verifiable by measuring optical path length using a scanning optical coherence tomography device.

Various alternate embodiments are taught, as can be seen by reference to the figures included herewith.

BRIEF DESCRIPTION OF THE DRAWINGS

The drawings provided as an aid to understanding the invention are.

DETAILED DESCRIPTION OF A PREFERRED EMBODIMENT

Figure 1:
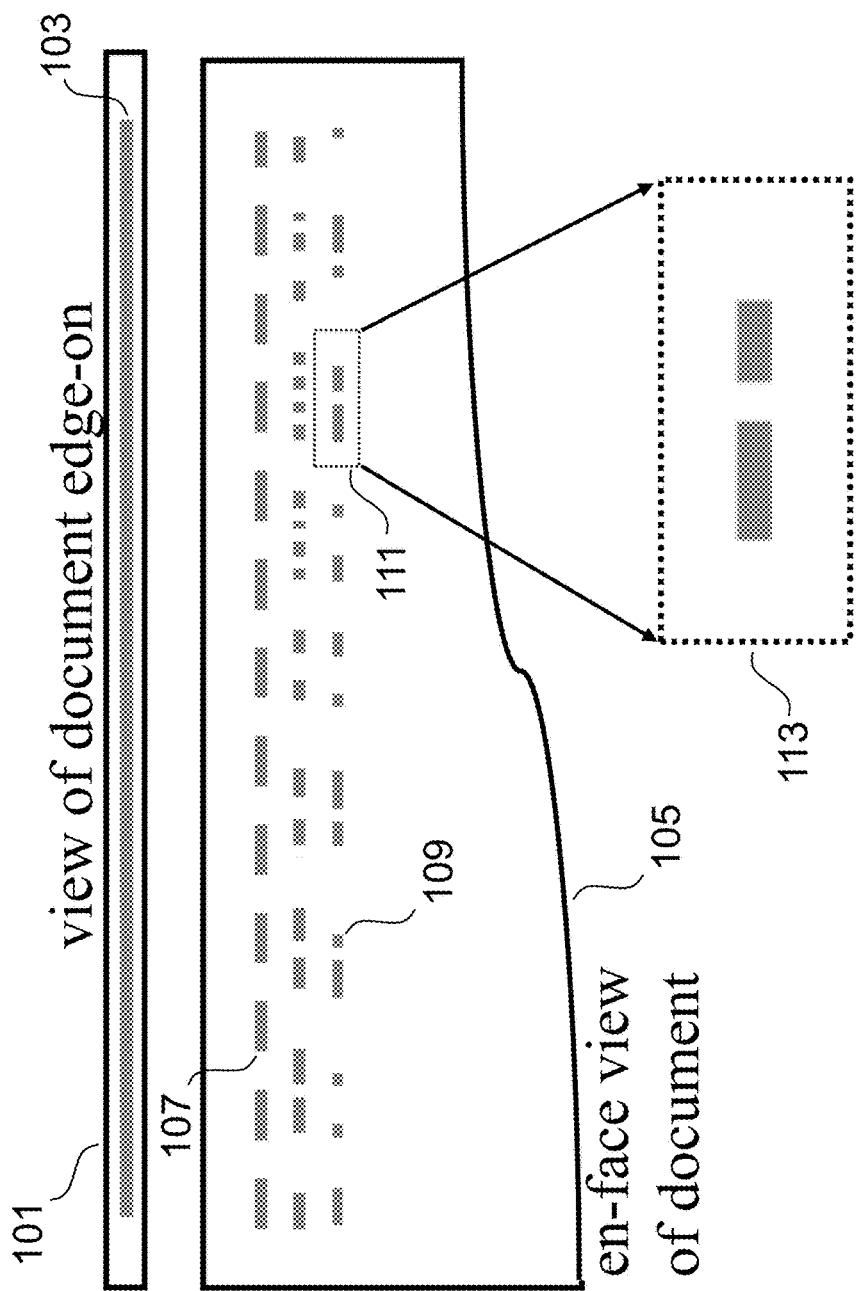
FIG. 1 is an illustration of an edge-on or side view of a document depicting the location of the embedded data layer according to the invention. It also depicts an en-face view of the document depicting typical data mark and space sequences.

The preferred embodiment of FIG. 1 illustrates an edge-on or side view 101 of a document depicting the location of the embedded data layer 103. It also depicts an en-face view 105 of the document depicting the spatial outline of typical data mark and space sequences. Mark 107 is an outline of one mark of a repetitive mark-space sequence used for registration. Below the registration mark-space sequence are two data carrying mark-space sequences.

Data can be encoded on the mark-space sequences by conventional data encoding techniques such as a run-length encoding technique as used, for example, encoding data on a DVD optical disc. Data integrity can be enhanced by the inclusion of error correction code-words, such as one or two dimensional Reed-Solomon error correction code-words.

An example of a short mark is depicted as mark 109 while region 111 depicts two different length marks separated by a short space and preceded and followed by spaces. An expanded view of this mark-space sequence is depicted in the dashed rectangle 113.

Figure 2:
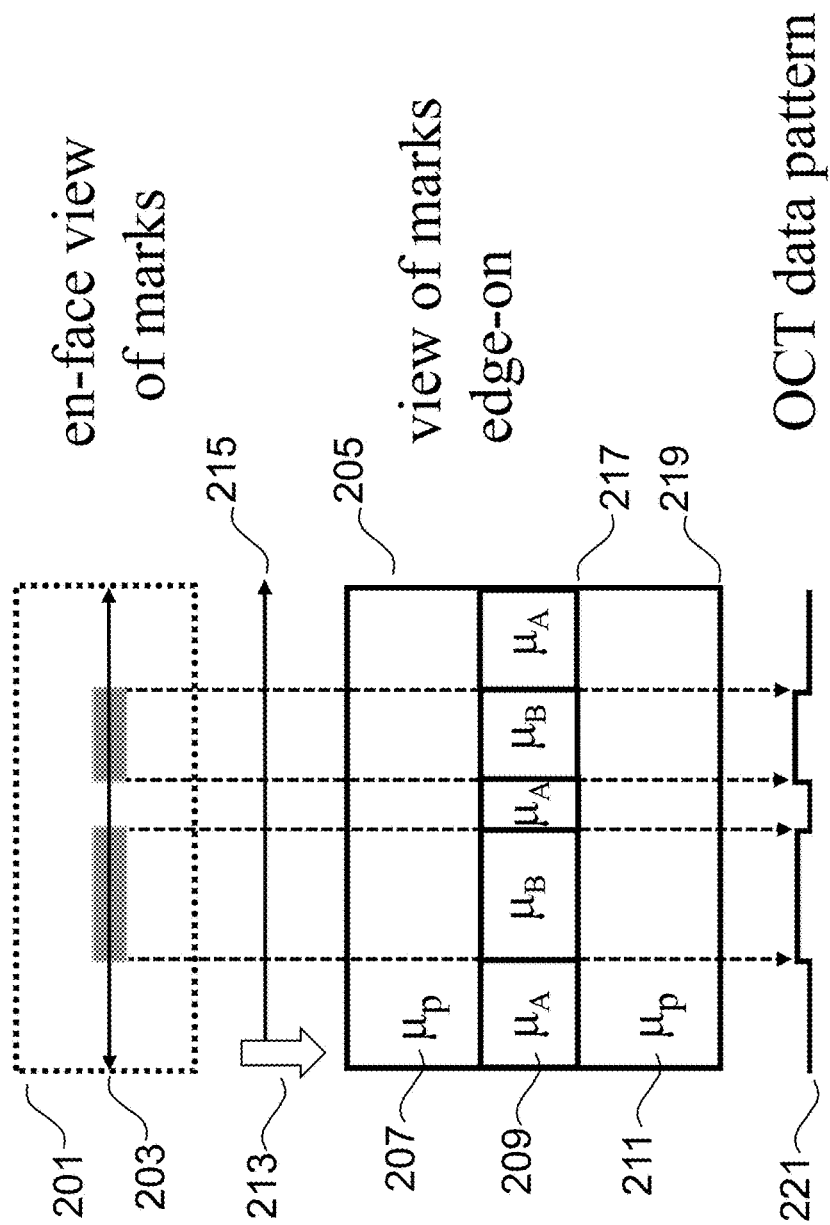
FIG. 2 depicts a short mark-space sequence; a detailed edge-on view of the mark-space sequence showing regions of different refractive index; and the associated data pattern.

FIG. 2 again depicts an en-face view of the mark-space sequence 201 with a double arrow 203 indicating the location of the cross-sectional or edge-on view of the same region 205 of the document. The detailed edge-on view 205 of the mark-space sequence shows a top region 207 of paper (or the material of the document, which material is also referred to as the base document).

The region 207 is the top layer of the paper and has a refractive index $\mu_p$ while the data layer 209 has alternating regions of two different refractive indices $\mu_A$ and $\mu_B$ corresponding to spaces and marks. The bottom layer of the paper 211 typically has the same refractive index $\mu_p$ as the top layer 207, although, if useful it could be a different refractive index.

An OCT probe beam indicated by 213 that acquires depth scans of the paper, where such depth scans are in the direction indicated by the block arrow 213 and where the optical probe beam also scans the paper in a lateral direction indicated by the arrow 215.

The data layer 209 has alternating regions of two different refractive indices $\mu_A$ and $\mu_B$ corresponding to spaces and marks, the optical thickness of the regions corresponding to the marks and the spaces. This causes the optical path-lengths of the alternating regions to be different, which causes the apparent distance to the layer boundary 217 to vary depending on whether a space or a mark region is above it.

Similarly the apparent distance to the bottom surface of the paper 219 varies depending on whether a space or a mark region is above the bottom layer 211. The resultant optical path-length related data signal, depicted as 221, can be readily extracted from the interference signal or signals from a scanning OCT system.

A practical example of such data encoded paper would be the three layers 207, 209 and 211 all being paper, but with the center layer 209 having holes where the spaces of the mark-space array are located. The layers are bonded together with a bonding material with a refractive index different from the paper, that the fills the spaces.

Figure 3:
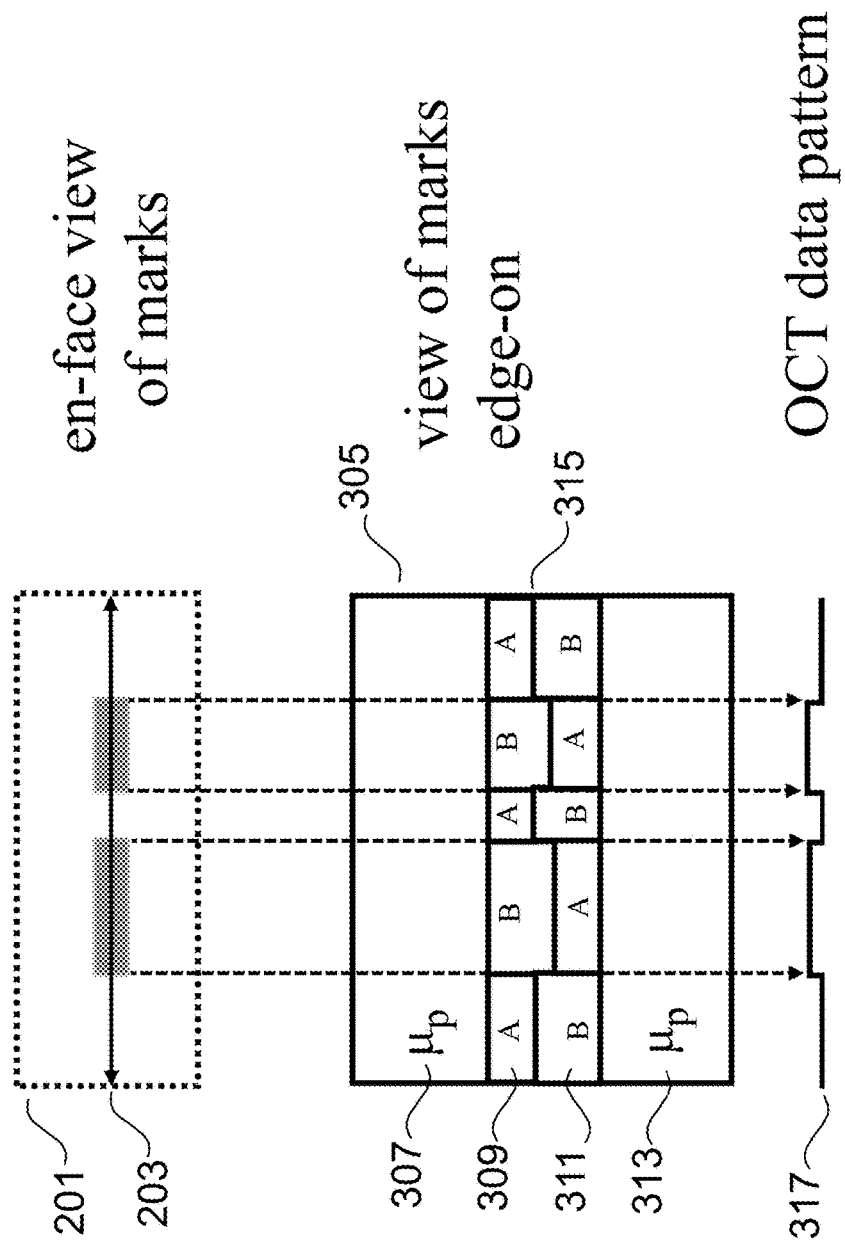
FIG. 3 depicts the short mark-space sequence of FIG. 2; a detailed edge-on view of the mark-space sequence showing an alternate embodiment of the regions of different refractive index; and the associated data pattern.

An alternate embodiment is depicted in FIG. 3 where the edge-on view 305 depicts a top paper layer 307 as before, but with the data layer consisting of regions 309 with alternating values of refractive index, indicated by A and B, with a complimentary layer 311 of alternating values of refractive index, indicated by B and A. The bottom layer 313 is as before.

In this embodiment the optical path-length to the boundary 315 varies with the different refractive indices and can be scanned by an OCT system to generate the data signal 317 from processed interference signals. This embodiment has the advantage that the total optical thickness of the paper is substantially the same at any point.

Figure 4:
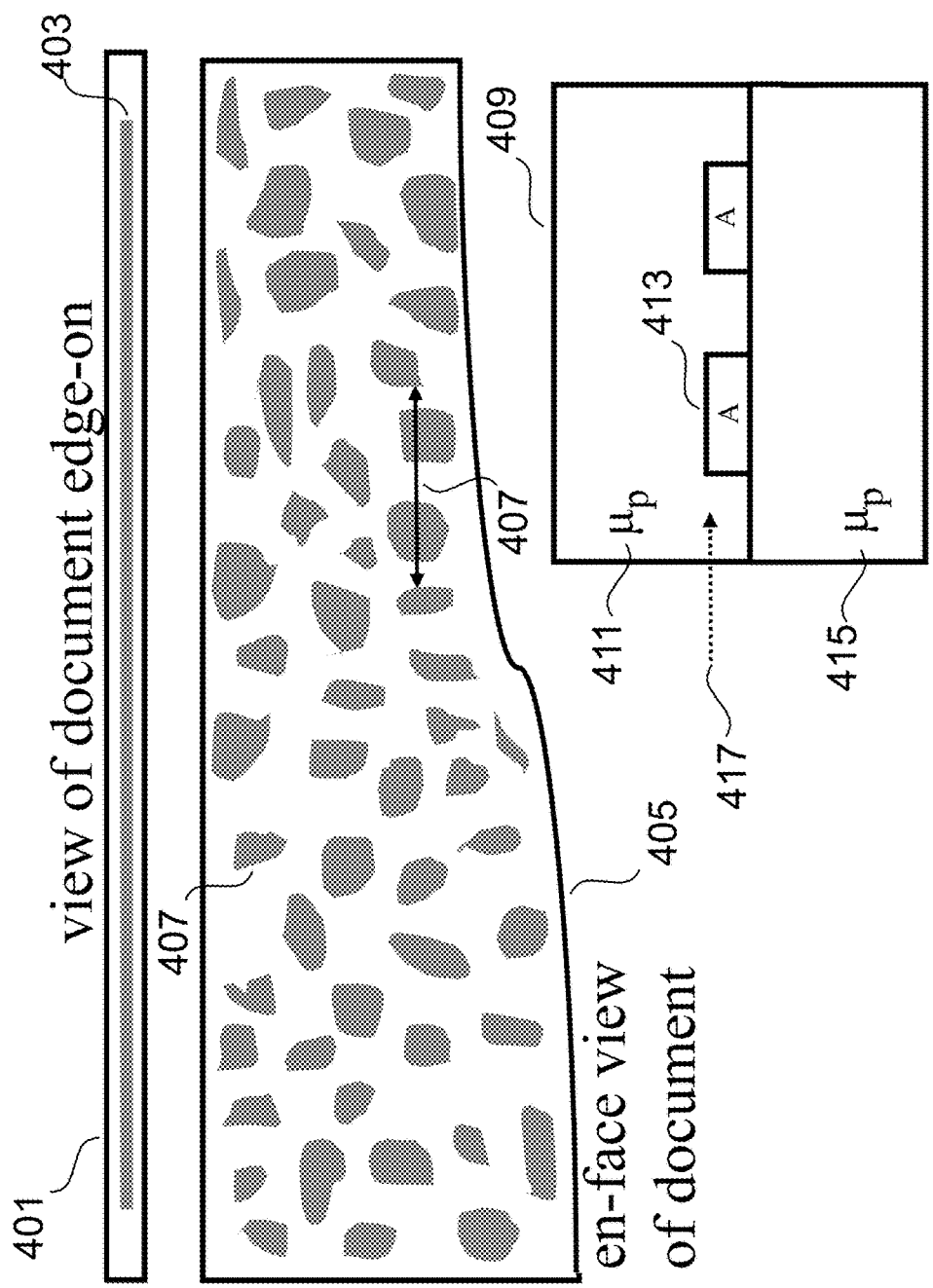
FIG. 4 illustrates the data layer in a document and also illustrates an en-face view of the document depicting randomly spatially distributed data mark and space regions.

An alternate embodiment is illustrated in FIG. 4 where an edge-on view 401 of paper depicts the data layer 403. An en-face view 405 depicts the locations of regions of different refractive index(s), with randomly varying shape, that are distributed randomly through-out the paper (or base document).

In one embodiment the regions of different refractive index consist of adhesive or bonding material that has a refractive index different from the refractive index of the paper. The irregular shapes and random distribution are a consequence of the manufacturing and bonding process of the two components of the paper.

A detailed view of the cross-section of a region indicated by 407 is depicted in 409 where the top portion 411 of the paper has voids, one of which is indicated by 413, which are filled by the adhesive or bonding material with refractive index $\mu_A$ different from the refractive index $\mu_p$ of the paper. Also depicted is the bottom portion 415 of the paper which also has a refractive index $\mu_p$.

OCT depth scans of the paper are processed to generate a data pattern at a depth indicated by the dashed arrow 417. The voids, such as 413, that are filled with the bonding material are either a natural consequence of the paper manufacturing process or embossed by a template with a pseudo-random pattern.

In another embodiment a spatially aligned pattern of voids is imposed or embossed on one portion of the paper to generate a spatially aligned data pattern based on voids filled with bonding material (and the spaces between them).

In another embodiment, the paper (or base document) consists of one or more layers and the random data pattern is a consequence of randomly distributed structural elements that are generated by the manufacturing process, and where such structural elements are discernable by an OCT system.

Aligned data patterns provide added security against counterfeiting of legal documents, such as bank notes, by including an OCT scanner in bank note readers. In one embodiment where one or more data sequences are aligned with known locations on the document, the additional security resides in the difficulty in reproducing the paper with these security marks included.

Such data sequences are very robust, availing of conventional channel coding, such as (2, 10) run length limited coding and conventional error correction techniques, such as Reed Solomon error correction code-words, similar to those of a DVD disc data sequence.

In another embodiment, OCT is used to scan the complete document and thereby acquire a complete volume image of the scattering properties of the document. Random structural elements provide the equivalent of a 3D fingerprint of the document.

Using a manufacturing process that ensures such structural elements are randomly distributed ensures each 3D fingerprint is unique and extremely difficult to counterfeit. Here the additional security resides in the difficulty in reproducing the document with the same 3D fingerprint.

Various security systems can be devised based on combinations of imposed aligned data mark sequences and one or more segments of the random 3D fingerprint. This general approach is enabled by the ubiquitous availability of a low cost OCT scanner.

For example a bank note including one or more data sequences, discernable only by an OCT reader are embedded in the structure of the paper aligned with known locations on the bank note. The authenticity of the bank note is determinable by an OCT scanner that is installed in a conventional bank note analyzer where such an OCT scanner has access to information about the embedded data.

In some embodiments the information about the embedded data available to the OCT scanner is the error corrected data. In other embodiments the information about the embedded data available to the OCT scanner is a hash of the error corrected data.

Additionally details of the location and 3D image of a small portion of the 3D fingerprint of the paper of the bank note is available to the OCT scanner.

In some embodiments the particular small portion of the 3D fingerprint of the paper of the bank note used in the above manner is periodically changed to a different location on the bank note.

Many variations of the above embodiments are possible. The embodiments are applicable to documents other than bank notes, such as credit cards, driving licenses, passports, wills property titles, etc. The scope of this invention should be determined with reference to the description and the drawings along with the full scope of equivalents as applied thereto.

I claim:

1. A method of uniquely identifying a document of interest, comprising the steps of:

a) embedding within the subsurface of said document a layer at a predetermined depth, said subsurface layer consisting of a plurality of regions wherein said regions alternate between regions having a first refractive index and regions having a second refractive index, where said first and said second refractive indexes are not equal to each other;

b) scanning said document using optical coherence tomography; and c) detecting a layer boundary of said subsurface layer wherein the optical path length to a layer boundary for said regions with a first refractive index have a first value, and wherein the optical path length to a layer boundary of said regions of said second refractive index have a second value, and where said first value does not equal said second value, so that the detected layer boundary constitutes a data pattern that uniquely identifies said document of interest.

2. A method of uniquely identifying a document of interest, said method comprising the steps of:

a) embedding within the sub surface of said document at least two layers each at a predetermined depth, wherein a first layer is a data layer consisting of a plurality of regions wherein said regions alternate between a first refractive index and a second refractive index—, and wherein a second layer likewise consists of a plurality of regions alternating between said first refractive index and said refractive index and where the location of each said region is complementary to said data layer such that complementary to said data layer so that the data layer and the complementary layer together result in a constant total optical thickness;

b) scanning said document using optical coherence tomography; and c) measuring an optical path length data signal obtained from said at least two subsurface layers, so that a detected optical path length data pattern from a region between said first layer and said second layer uniquely identifies said document of interest.

\* \* \* \* \*